(12) United States Patent
Biglia

(10) Patent No.: US 10,760,118 B2
(45) Date of Patent: Sep. 1, 2020

(54) METHOD FOR DNA AMPLIFICATION WITH A BLOCKING OLIGONUCLEOTIDE

(71) Applicant: QIAGEN MARSEILLE, Marseilles (FR)

(72) Inventor: Olivier Biglia, Marseilles (FR)

(73) Assignee: QIAGEN GMBH, Hilden (DE)

( * ) Notice: Subject to any disclaimer, the term of this patent is extended or adjusted under 35 U.S.C. 154(b) by 98 days.

(21) Appl. No.: 14/785,747

(22) PCT Filed: Apr. 29, 2014

(86) PCT No.: PCT/EP2014/058685
§ 371 (c)(1),
(2) Date: Oct. 20, 2015

(87) PCT Pub. No.: WO2014/177540
PCT Pub. Date: Nov. 6, 2014

(65) Prior Publication Data
US 2016/0076089 A1 Mar. 17, 2016

(30) Foreign Application Priority Data

Apr. 29, 2013 (EP) .................................. 13305566

(51) Int. Cl.
*C12Q 1/6858* (2018.01)
*C12Q 1/6853* (2018.01)
*C12Q 1/6848* (2018.01)
*C12N 1/00* (2006.01)

(52) U.S. Cl.
CPC ......... *C12Q 1/6858* (2013.01); *C12Q 1/6848* (2013.01); *C12Q 1/6853* (2013.01)

(58) Field of Classification Search
CPC ........ C12Q 2525/161; C12Q 2525/186; C12Q 2535/131; C12Q 2537/161; C12Q 2537/163; C12Q 2549/126; C12Q 1/6848; C12Q 1/6853; C12Q 1/6858
See application file for complete search history.

(56) References Cited

U.S. PATENT DOCUMENTS

| 6,387,652 B1 | 5/2002 | Haugland et al. | |
|---|---|---|---|
| 2013/0149695 A1 * | 6/2013 | Lee ..................... | C12Q 1/6858 435/5 |

FOREIGN PATENT DOCUMENTS

WO   WO-2011136462 A1 * 11/2011 ....... C12Q 2537/163

OTHER PUBLICATIONS

Parsons, B.L. et al., Env. Mol. Mutagen., vol. 32, pp. 200-211 (1998).*

(Continued)

*Primary Examiner* — Teresa E Strzelecka
(74) *Attorney, Agent, or Firm* — Ballard Spahr LLP

(57) ABSTRACT

The invention relates to an in vitro method for selectively amplifying a target DNA sequence from a nucleic acid sample, which method comprises running a PCR amplification of a nucleic acid sample suspected of comprising at least one target DNA sequence that differs from a reference DNA sequence at at least one predetermined target mutation site; wherein said method employs a blocking oligonucleotide complementary to a portion of the reference DNA sequence comprising the target mutation site, with the exception of a least one mismatch outside the target mutation site.

17 Claims, 1 Drawing Sheet

Specification includes a Sequence Listing.

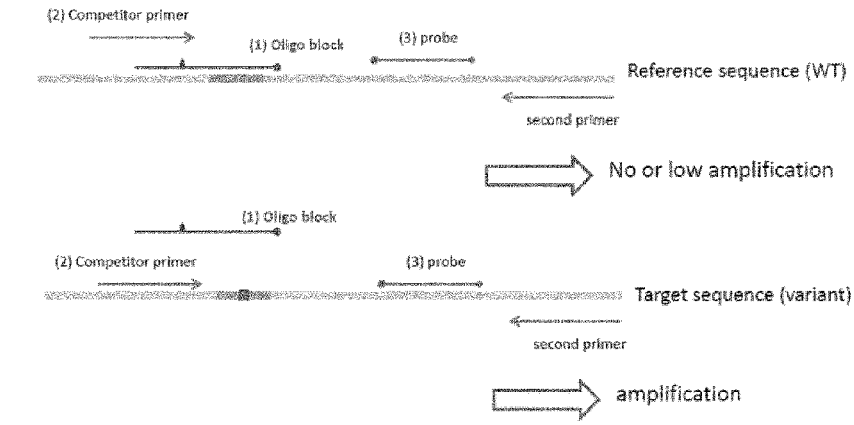

(56) References Cited

OTHER PUBLICATIONS

Ntziora, F. et al., J. Clin. Microbiol., vol. 47, pp. 2544-2550 (2009).*
Lee, S-T. et al., J. Mol. Diagn., vol. 13, pp. 657-668 (2011).*
Gibson, N.J., Clin. Chim. Acta, vol. 363, pp. 32-47 (2006).*
Guo, Z. et al., Enhanced discrimination of single nucleotide polymorphisms by artificial mismatch hybridization, Nature Biotechn., vol. 15, pp. 331-336 (Year: 1997).*
Altschul et al., "Basic local alignment search tool." J Mol Biol. (1990); 215(3):403-10.
Altschul et al., "Gapped BLAST and PSI-BLAST: a new generation of protein database search programs." Nucleic Acids Res. (1997); 25(17):3389-402.
Dominguez P.L. et al., "Wild-type blocking polymerase chain reaction for detection of single nucleotide minority mutations from clinical specimens." Oncogene (2005); 24:6830-6834.
Jang, Mi-Ae et al., "Identification of a Rare 3 bp BRAF Gene Deletion in a Thyroid Nodule by Mutant Enrichment with 3'-Modified Oligonucleotides Polymerase Chain Reaction." Ann Lab Med. (2012); 32(3): 238-241.
Lee, Seung-Tae et al., "Mutant Enrichment with 3'-Modified Oligonucleotides a Practical PCR Method for Detecting Trace Mutant DNAs." J Mol Diagn. (2011); 13(6):657-668.

Li J. et al., "Replacing PCR with COLD-PCR enriches variant DNA sequences and redefines the sensitivity of genetic testing." Nat Med. (2008); 14:579-584.
Parsons, B.L. et al., "Detection of basepair substitution mutation at a frequency of $1 \times 10(-7)$ by combining two genotypic selection methods, MutEx enrichment and allele-specific competitive blocker PCR." Environ Mol Mutagene. (1998); 32(3):200-211.
Sun, X. et al., "Detection of tumor mutations in the presence of excess amounts of normal DNA." Nature Biotechnol. (2002) 20:186-189.
Wetmur, J. G., "DNA probes: applications of the principles of nucleic acid hybridization." Crit Rev Biochem Mol Biol (1991) 26: 227-259.
International Search Report and Written Opinion dated Jul. 23, 2014 by the International Searching Authority for PCT Application No. PCT/EP2014/058685 on Apr. 29, 2014 and published as WO 2014/177540 on Nov. 16, 2014 (Applicant—Qiagen Marseille; Inventor—Olivier Biglia) (9 pages).
International Preliminary Report on Patentability dated Nov. 3, 2015 by the International Searching Authority for PCT Application No. PCT/EP2014/058685 on Apr. 29, 2014 and published as WO 2014/177540 on Nov. 16, 2014 (Applicant—Qiagen Marseille; Inventor—Olivier Biglia) (6 pages).

* cited by examiner

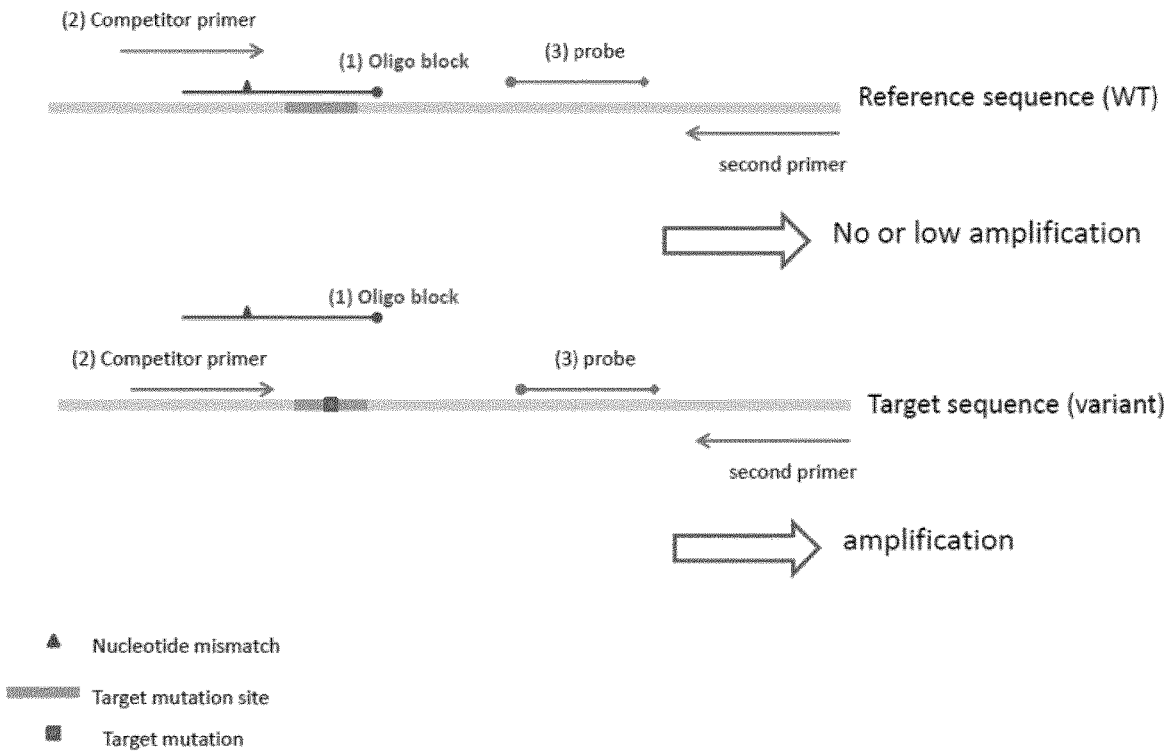

FIGURE 1

R132wt (seq ID no : 1)
GAGTGGATGGGTAAAACCTATCATCATAGGT*CG*TCATGCTTATGGGGATCAAGTAAGTCATGTTGGCA R132H (seq ID no : 2)
　　　　　GAGTGGATGGGTAAAACCTATCATCATAGGTCATCATGCTTATGGGGATCAAGTAAGTCATGTTGGCA R132C (seq ID no : 3)
　　　　　GAGTGGATGGGTAAAACCTATCATCATAGGTTGTCATGCTTATGGGGATCAAGTAAGTCATGTTGGCA R132S (seq ID no : 4)
　　　　　GAGTGGATGGGTAAAACCTATCATCATAGGTAGTCATGCTTATGGGGATCAAGTAAGTCATGTTGGCA R132G (seq ID no : 5)
　　　　　GAGTGGATGGGTAAAACCTATCATCATAGGTGGTCATGCTTATGGGGATCAAGTAAGTCATGTTGGCA R132L (seq ID no : 6)
　　　　　GAGTGGATGGGTAAAACCTATCATCATAGGTCTTCATGCTTATGGGGATCAAGTAAGTCATGTTGGCA R132V (seq ID no : 7)
　　　　　GAGTGGATGGGTAAAACCTATCATCATAGGTGTTCATGCTTATGGGGATCAAGTAAGTCATGTTGGCA

FIGURE 2

METHOD FOR DNA AMPLIFICATION WITH A BLOCKING OLIGONUCLEOTIDE

CROSS-REFERENCE TO RELATED APPLICATIONS

The present application is a National Stage Entry of PCT Application No. PCT/EP2014/058685, filed Apr. 29, 2014, which claims priority to EP Application No. 13305566.5, filed Apr. 29, 2013, both of which are hereby incorporated herein by their reference in their entirety.

REFERENCE TO SEQUENCE LISTING

The Sequence Listing submitted herein on Oct. 20, 2015, as a text file named "17104_0052U1_Sequence_Listing.txt," created on Oct. 14, 2015, and having a size of 4,665 bytes is hereby incorporated by reference pursuant to 37 C.F.R. § 1.52(e)(5).

FIELD OF THE INVENTION

The invention pertains to improvements to the amplification, enrichment, and/or detection of variant target sequences, e.g. mutations, in nucleic acid samples.

BACKGROUND OF THE INVENTION

A commonly encountered situation in genetic analysis entails the need to identify a low percent of variant DNA sequences ('target sequences') in the presence of a large excess of non-variant sequences ('reference sequences'). As an example, sensitive and confident detection of trace disease-associated mutant alleles among an excess of normal alleles has become essential for early or confirmatory diagnoses, therapeutic decisions, disease monitoring, and prognostic stratification. However balancing high sensitivity with reliability and practicality of use remains challenging.

Sanger sequencing, the robust standard method, can only detect approximately 10-20% of mutant alleles in a background of normal alleles, whereas other, more sensitive, PCR-based assays such as restriction fragment length polymorphism, amplification refractory mutation system PCR (ARMS-PCR), denaturing high-performance liquid chromatography, and real-time PCR could be more limited. Amplification refractory mutation system PCR, the most widely used method, is an amplification strategy in which a PCR primer is designed to discriminate among templates that differ by a single nucleotide residue. This method is simple and time efficient but is sequence-specific, requiring to know the mutation to detect beforehand, and sometimes produces serious false-positive results.

There have been efforts to develop new molecular technologies aimed at overcoming the inherent drawbacks of prior methods. There has been particular interest in the innovation of PCR stages that enable nondestructive selection and enrichment of mutant alleles, as this can improve sensitivity and credibility of downstream assays, such as standard sequencing analysis. These recent enrichment PCR techniques include PCR clamping mediated by peptide nucleic acid (PNA) (Sun et al, 2002) or locked nucleic acid (LNA) (Dominguez et al, 2005), and co-amplification at lower denaturation temperature PCR (Li et al, 2008). Each technique has its own strengths and limitations in regard to the cost, availability, or enrichment efficiency.

In Lee et al, 2011, the authors describe a simple and practical enrichment technique, called mutant enrichment with 3'-modified oligonucleotides (MEMO). The concept of this technique is similar to that of PNA/LNA-mediated PCR clamping, but the PNA or LNA is replaced by 3'-modified oligonucleotides that are much less expensive and are easy to design. Briefly, two generic primers and one blocking primer constitute the PCR reaction mixture. On the 3'-end of the blocking primer, an extension-inhibiting compound such as a C3 spacer, a C6 amine, or a phosphate is attached so that PCR cannot extend the DNA via the blocking primer. The blocking primer encompasses the target mutation site and is complementary to the wild-type sequence. One of the two generic primers overlaps with the blocking primer by several bases, neighboring the target mutation site, and thus is in competition with the blocking primer. The DNA binding of the blocking primer, which is designed to have a higher melting temperature and to be used in a higher concentration in the reaction mixture than the generic primer with which it competes, dominates for wild-type sequence, whereas its affinity for mutant sequences is markedly reduced due to mismatches. The loss of competition of the blocking primer enables selective amplification of mutant sequences by the generic primer pair.

This MEMO-PCR was employed to identify a rare 3 bp BRAF gene deletion in a thyroid nodule (Jang et al, 2012).

However there remained a need for a method of detection with improved specificity, in particular when the variant target sequences carry nucleotide substitution(s). Indeed such sequences had been poorly discriminated so far.

SUMMARY OF THE INVENTION

The invention now provides an improved method for detecting variant DNA sequences ('target sequences'), especially, but not limited to, in the presence of an excess of non-variant or wild-type (WT) sequences ('reference sequences').

The method of the invention is an in vitro method for selectively amplifying a target DNA sequence from a nucleic acid sample, which method comprises running a PCR amplification of a nucleic acid sample suspected of comprising at least one target DNA sequence that differs from the reference DNA sequence at at least one predetermined target mutation site; wherein said method employs a blocking oligonucleotide complementary to a portion of the reference DNA sequence comprising the target mutation site, with the exception of a least one mismatch outside the target mutation site.

More particularly, the invention provides an in vitro method for selectively amplifying a target DNA sequence from a nucleic acid sample, which method comprising a. providing a nucleic acid sample suspected of comprising at least one target DNA sequence that differs from a reference DNA sequence at at least one target mutation site;

b. adding:
  i) a forward primer oligonucleotide and a reverse primer oligonucleotide, which are fully complementary with a portion of the reference DNA sequence surrounding the target mutation site,
  ii) a blocking oligonucleotide, which is designed to compete with one of the primer oligonucleotides and is modified so that it cannot be extended by polymerase, so as to form a reaction mixture;

c. subjecting the reaction mixture to amplification by polymerase chain reaction (PCR), whereby the primer oligonucleotides are extended so as to selectively amplify said target DNA sequence;

wherein said method is characterized in that the blocking oligonucleotide is complementary to a portion of the reference DNA sequence comprising the target mutation site, but comprises at least one mismatch with the reference DNA sequence outside the target mutation site.

The target mutation may comprise a substitution of one or several nucleotides, a deletion of one or several nucleotides, or an insertion of one or several nucleotides. Most preferably it is or comprises a single nucleotide substitution.

The method is an improvement of the known PCR clamping methods.

According to the present invention, it was found that adding a sequence mismatch in the blocking oligonucleotide significantly improves the specificity of detection of the target sequence. Especially, the addition of a sequence mismatch dramatically improves the discrimination of variant sequences characterized by nucleotide substitution(s).

The method of the invention is particularly useful for distinguishing nucleic acid samples that comprise a target sequence, from nucleic samples that comprise a reference sequence, e.g. for diagnosis purposes.

The invention further provides a method for detecting and/or determining a target mutation in a nucleic acid sample, which method comprises subjecting a nucleic acid sample suspected of comprising at least one target DNA sequence that differs from a reference DNA sequence at at least one target mutation site, to the amplification method as described herein, and detecting and/determining the target mutation of the target DNA sequence that has been amplified.

The method may thus comprise comprising determining the target mutation of the target DNA sequence that has been amplified by using one or more of the methods selected from the group consisting of: MALDI-TOF, high resolution melting (HR-Melting), Di-deoxy-sequencing, Single-molecule sequencing, pyrosequencing, Second generation high-throughput sequencing, Single-Strand Conformation Polymorphism (SSCP), restriction fragment length polymorphism (RFLP), Denaturing High Performance Liquid Chromatography (dHPLC), digital PCR, ARMS-PCR and quantitative-PCR.

BRIEF DESCRIPTION OF THE DRAWINGS

FIG. 1 is a schematic representation of the method of the invention, using a 3' modified Oligo block containing a sequence mismatch. In presence of wild-type sequence, the Oligo block hybridizes (1) its target sequence, leading to PCR amplification inhibition. In presence of any sequence variation(s), the competitor primer (2) preferentially binds to the target sequence, leading to a specific amplification of the variant sequence, which can, for instance, be monitored by fluorescence emission from a hydrolysis probe (3).

FIG. 2 shows the sequence and position of the IDH1 R132 mutations. Underlined in the wild-type sequence of the IDH1 gene are the two nucleotides (within the R132 codon) that can be substituted by other nucleotides in the variant sequences. For each variant sequence, the corresponding substituted nucleotide is shown in bold.

DETAILED DESCRIPTION

Definitions

As used herein, the term "amplifying" a target sequence refers to increasing the amount of a target sequence. The term "selectively amplifying" means that the target sequence only (or substantially only) is amplified. The term "enriching" more particularly means increasing the ratio of target sequence relative to the corresponding reference sequence in a sample. For example, where the ratio of target sequence to reference sequence is initially 5 percent to 95 percent in a sample, the target sequence may be preferentially amplified in an amplification reaction so as to produce a ratio of 70 percent target sequence to 30 percent reference sequence. Thus, there may be a 14-fold enrichment of the target sequence relative to the reference sequence.

As used herein the term "target sequence" refers to the sequence of interest, to be detected and amplified. The target sequence is typically at least 50 percent homologous, to the corresponding reference sequence, preferably at least 60% homologous, still preferably at least 70% homologous, but must differ by at least one nucleotide from the reference sequence. Target sequences are amplifiable via PCR with the same pair of primers as those used for the reference sequence. In a particular embodiment, the target sequence is less prevalent in a nucleic acid sample than a corresponding reference sequence. The target sequence preferably makes-up less than 50 percent of the total amount of reference sequence+target sequence in a sample. The target sequence may be a mutant allele. For example, a sample (e.g., blood sample) may contain numerous normal cells and few cancerous cells. The normal cells contain non-mutant or wild-type alleles, while the small number of cancerous cells contains somatic mutations. In this case the mutant is the target sequence while the wild-type sequence is the reference sequence.

As used herein, the term "reference sequence" means a sequence that could be amplified with the same primer pair as for the target sequence, but the amplification of which is not desired. Such sequence encompasses a non-variant or wild-type sequence. Preferably the "reference sequence" is fully, or at least partly, known. In a particular embodiment, the term "reference sequence" refers to a nucleic acid that is more prevalent in a nucleic acid sample than a corresponding target sequence. The reference sequence preferably makes-up over 50 percent of the total reference sequence+target sequence in a sample. Preferably the reference sequence is expressed at the RNA and/or DNA level 10×, 15×, 20×, 25×, 30×, 35×, 40×, 45×, 50×, 60×, 70×, 80×, 90× 100×, 150×, 200× or more than the target sequence.

As used herein, the term "wild-type" refers to the most common polynucleotide sequence or allele for a certain gene in a population. Generally, the wild-type allele will be obtained from normal cells.

As used herein, the term "target mutation" refers to a nucleotide change (i.e., a single or multiple nucleotide substitution, deletion, or insertion) in a nucleic acid sequence. A nucleic acid which bears a mutation has a nucleic acid sequence (mutant allele) that is different in sequence from that of the corresponding wild-type polynucleotide sequence. The invention is broadly concerned with somatic mutations and polymorphisms. The methods of the invention are especially useful in selectively amplifying or enriching a mutant allele which contains changes at 1 to 10 nucleotide positions, although is useful even with a higher number of sequence changes. A mutant allele will typically be obtained from diseased tissues or cells and is associated with a disease state. The term "target mutation site" means a region of the DNA sequence that comprises or is suspected or likely to comprise a target mutation. Although the nature of the target mutation itself, or the exact location, may be unknown, the target mutation site is defined or predetermined. Generally it is a region of about 5 to about 30 nucleotides comprising the target mutation. In a particular embodiment, the mutation may be a single nucleotide substitution, the exact location of which is known, and the target mutation site may then be the position of the mutated nucleotide itself.

As used herein the term "melting temperature" or "$T_m$" refers to the temperature at which a polynucleotide dissociates from its complementary sequence. Generally, the $T_m$ may be defined as the temperature at which one-half of the Watson-Crick base pairs in a double stranded nucleic acid molecule are broken or dissociated (i.e., are "melted") while the other half of the Watson-Crick base pairs remain intact in a double stranded conformation. In other words the $T_m$ is defined as the temperature at which 50 percent of the nucleotides of two complementary sequences are annealed (double strands) and 50 percent of the nucleotides are denatured (single strands). $T_m$ therefore defines a midpoint in the transition from double-stranded to single-stranded nucleic acid molecules (or, conversely, in the transition from single-stranded to double-stranded nucleic acid molecules). The $T_m$ can be estimated by a number of methods, for example by a nearest-neighbor calculation as per Wetmur 1991 and by commercial programs including Oligo™ Primer Design and programs available on the internet. Alternatively, the $T_m$ can be determined through actual experimentation. For example, double-stranded DNA binding or intercalating dyes, such as Ethidium bromide or SYBR-green (Molecular Probes) can be used in a melting curve assay to determine the actual $T_m$ of the nucleic acid. Additional methods for determining the $T_m$ of a nucleic acid are well known in the art.

As used herein, "homology" refers to the subunit sequence similarity between two polymeric molecules, e.g., two polynucleotides. An example of an algorithm that is suitable for determining percent sequence identity and sequence similarity are the BLAST and BLAST 2.0 algorithms, which are described in Altschul et al, 1997 and Altschul et al, 1990, respectively. Software for performing BLAST analyses is publicly available through the National Center for Biotechnology Information (http://www.ncbi.nlm.nih.gov/).

Nucleic Acid Sample

As used herein, "sample" refers to any substance containing or presumed to contain a nucleic acid of interest (target and/or reference sequences) or which is itself a nucleic acid containing or presumed to contain a target nucleic acid of interest. The term "sample" thus includes a sample of nucleic acid, cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules. Formalin fixed, paraffin-embedded (FFPE) tissues are encompassed.

The target (and reference sequences) can be obtained from a variety of sources including, genomic DNA, complementary DNA (cDNA), viral DNA, mammalian DNA, fetal DNA or bacterial DNA. In one embodiment, a nucleic acid sample utilized in the method of the invention generally comprises genomic DNA, e.g. genomic DNA having a target and reference sequence. Genomic DNA can be isolated from blood, tissues or cells according to well-known methods, e.g. by using commercial kits (such as QIAmp DNA extraction kit by Qiagen, for extraction from FFPE or blood). In another embodiment the nucleic acid source can be RNA, from which cDNA is produced, by standard methods.

In a particular embodiment, the nucleic acid sample of the method of the invention comprises target and/or reference sequences that were previously amplified in a nucleic acid amplification reaction. The skilled artisan will appreciate that there are many methods available to amplify a nucleic acid.

While the reference sequence is generally the wild-type allele and the target sequence is the mutant allele, the reverse may also be true. The mutant allele may include any one or more nucleotide deletions, insertions or alterations. In some embodiments, the mutant allele is a somatic mutation.

Reaction Mixture

The method of the invention employs two primers that anneal to opposite strands of the target and reference sequences so as to form an amplification product during a PCR reaction. The amplicon size is typically between about 60 to about 500 bp, preferably about 80 to about 250 bp.

The primer oligonucleotides generally comprise from 10 to 40 nucleotides, preferably from 10 to 30 nucleotides, still preferably from 15 to 25 nucleotides. The primer oligonucleotides preferably have a Tm around 56-64° C. The primer oligonucleotides are 100% complementary to a portion of the reference and target sequence. Generally the primers are not modified at their 3' or 5' ends.

One of the primer oligonucleotide is the "competing" or "competitor" primer in the invention, i.e. it is intended to compete with a blocking oligonucleotide for binding to the reference or target sequence. Therefore the competing primer at least partly overlaps with the blocking oligonucleotide sequence, as explained below, As used herein, "blocking oligonucleotide" is an engineered single stranded nucleic acid sequence. The blocking oligonucleotide may be one of single stranded DNA, RNA, peptide nucleic acid or locked nucleic acid. Preferably it is a DNA oligonucleotide. The blocking oligonucleotide generally comprises from 10 to 40 nucleotides, preferably from 15 to 30 nucleotides.

The blocking oligonucleotide is modified so that it cannot be extended by polymerase.

In a preferred embodiment, a 3'-end on the blocking oligonucleotide is modified to inhibit extension by polymerase.

Such a blocking sequence can be synthesized by any known method. First, the reference blocking sequence can be made by direct synthesis using standard oligonucleotide synthesis methods that allow modification of the 3'-end of the sequence. The 3'-end may contain a phosphate group, an amino-group, a di-deoxy-nucleotide or any other moiety that blocks 5' to 3' polymerase extension. Alternatively, the reference blocking sequence can be made by polymerase synthesis during a PCR reaction that generates single stranded DNA as the end product.

Blocking the 3'-end of the blocking oligonucleotide can be accomplished in several ways well known to those skilled in the art. For example, a reaction with Terminal Deoxynucleotide Transferase (TdT) can be employed, in the presence of di-deoxy-nucleotides (ddNTP) in the solution, to add a single ddNTP to the end of the single stranded reference blocking sequence. ddNTPs serve to block polymerase extension. Alternatively, an oligonucleotide template complementary to the 3'-end of the blocking sequence can be used to provide a transient double stranded structure. Then, polymerase can be used to insert a single ddNTP at the 3'-end of the reference blocking sequence opposite the hybridized oligonucleotide.

For instance, the 3'-end of the blocking oligonucleotide may comprise a C3 spacer, a C6 amine or a phosphate group.

The "C3 spacer" modification adds a three carbon spacer to the 3' terminus of the oligonucleotide, which becomes e.g.

The C6 amine modification incorporates an amine functionality at the 3' terminus of an oligonucleotide.

The blocking oligonucleotide is designed to compete with of one the primer oligonucleotides.

The sequence of the blocking oligonucleotide thus overlaps with the sequence of one of the primer oligonucleotides. The overlap (i.e. the common sequence between the competitor primer and the blocking oligonucleotide) can comprise, or consist of, at least 30%, 40%, 50%, 60%, 70%, 80% or 85% of the blocking oligonucleotide. Or the overlap can comprise, or consist of, at least 5, 6, 7, 8, 9, 10, 11, 12, 13, or 14 nucleotides. The overlap does not comprise the target mutation site.

The blocking oligonucleotide sequence at least partly overlaps with the primer oligonucleotide it competes with, but is designed to have a higher melting temperature (Tm), (e.g. between about 1 to about 15° C. higher, preferably between about 1 to about 10° C. higher), and/or is added at a higher concentration than the primer oligonucleotide it competes with.

For example, the blocking oligonucleotide is added at a concentration that is at least twice, preferably at least three times, at least 4 times or at least 5 times higher than the concentration of the primer oligonucleotide it competes with.

The blocking oligonucleotide is complementary to a portion of the reference DNA sequence, which portion comprises the (non-mutated or wild-type) nucleotide(s) corresponding to the target mutation site. Said portion of the reference DNA sequence is identical to a corresponding portion of the target DNA sequence, except at the target mutation site.

In a preferred embodiment, the blocking oligonucleotide is designed so that the central part of its sequence binds the target mutation site of the reference or target DNA sequence.

The competing primer overlaps with the blocking oligonucleotide by several bases, neighboring the target mutation site.

According to the present invention, the blocking oligonucleotide yet comprises at least one nucleotide that is not complementary to the corresponding nucleotide on the reference or target DNA sequence. Of course it is to be understood that said nucleotide is not located at the target mutation site.

The nucleotide that is not complementary to the corresponding nucleotide on the reference or target DNA sequence is preferably a A or T nucleotide, rather than a G or C nucleotide.

This mismatch in the blocking oligonucleotide (i.e. said nucleotide(s) not complementary to the corresponding nucleotide(s) on the reference sequence) is preferably located upstream, from the target mutation site.

Still preferably, this mismatch may be located in a part of the blocking oligonucleotide that overlaps with the competing primer.

The binding of the blocking oligonucleotide dominates for reference (or wild-type) sequences over the binding of the competitor primer. Therefore, no PCR elongation of the reference sequence can occur.

In the presence of mutations in the target DNA sequence, the affinity of the blocking oligonucleotide for the mutant or variant sequences is markedly decreased due to the mismatches, and there is a preferential binding of the competitor primer, which allows PCR elongation. Therefore, there is a selective amplification of the target (mutant or variant) sequences by the primer pair (see FIG. 1).

Without being linked by any mechanism, the inventors believe that such mismatch destabilizes the binding of the blocking oligonucleotide, which results in preferential binding of the competing primer to target sequence, and hence a more discriminating amplification of the target sequence.

The reaction mixture typically comprises further ingredients, such as enzymes, bases (e.g. A, T, G, C) or oligonucleotides useful for implementing amplification or detection.

In particular the reaction mixture can include a nucleic acid polymerase, which is an enzyme that catalyzes the polymerization of nucleoside triphosphates. Generally, the enzyme will initiate synthesis at the 3'-end of the primer annealed to the target sequence, and will proceed in the 5'-direction along the template. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase. The term "nucleic acid polymerase" also encompasses RNA polymerases. If the nucleic acid template is RNA, then "nucleic acid polymerase" refers to an RNA-dependent polymerization activity, such as a reverse transcriptase.

For instance said reaction mixture may further contain a nucleic acid detection dye, such as fluorescent dyes (e.g. DAPI, Hoechst Dyes, PicoGreen, RiboGreen, OliGreen, and cyanine dyes such as YO-YO, ethidium bromide, and SybrGreen).

In a preferred embodiment, said reaction mixture may further contain a probe, preferably a labeled probe.

The probe advantageously does not overlap with the primers or the blocking oligonucleotide.

This is particularly useful for quantitative PCR (qPCR).

The probe is an oligonucleotide that anneals to a sequence on the target DNA found between the forward (5') and reverse (3') PCR primer binding sites. Tm of the probe is generally higher than Tm of the primers. A hydrolysis probe, such as a Taqman probe, is particularly advantageous. Such probes rely on the 5'-3' exonuclease activity of Taq polymerase, which degrades a hybridized non-extendible DNA probe during the extension step of the PCR. This probe is designed to hybridize to a region within the amplicon and is duel labeled with a reporter dye and a quenching dye. The close proximity of the quencher suppresses the fluorescence of the reporter dye. Once the exonuclease activity of Taq polymerase degrades the probe, the fluorescence of the reporter increases at a rate that is proportional to the amount of template present.

In a preferred embodiment, the probe can be labeled with a 5'-reporter dye (e.g., FAM, 6-carboxyfluorescein) and a 3'-quencher dye (e.g., TAMRA, 6-carboxytetramethylrhodamine) which quenches the emission spectra of the reporter dye as long as both dyes are in close proximity or attached to the probe. The probe signals the formation of PCR amplicons by a process involving the polymerase-induced nucleolytic degradation of the double-labeled fluorogenic probe that anneals to the target template at a site between the two primers recognition sequences. See, e.g. U.S. Pat. No. 6,387,652.

Amplification Reaction

The amplification according to the invention is performed by polymerase chain reaction (PCR).

In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers.

The PCR described herein is thus preferably repeated for two or more cycles, preferably from 10 to 50 cycles.

PCR is performed using template DNA (target and reference sequences) (at least 1 fg; more usefully, 1-1000 ng) and at least 7.5 pmol of oligonucleotide primers. A typical reaction mixture includes: 5 μl of DNA, 7.5 pmol of oligonucleotide primer, 12.5 μl of a 2× mastermix from the QuantiTect Probe PCR Kit and deionized water to a total volume of 25 μl. PCR is performed using a programmable thermal cycler.

According to the present invention, the primers are used in a concentration of about 100 to about 500 nM, preferably about 300 nM, while the blocking oligonucleotide is used at a concentration of about 1 to about 5 μM, preferably about 2 μM.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of skill in the art. An annealing temperature of between 30° C. and 72° C. is used. Initial denaturation of the template molecules normally occurs at between 92° C. and 99° C. for about 15 seconds, preferably for about 1 or 4 minutes to about 10-15 minutes, followed by 20-50 cycles consisting of denaturation (94-99° C. for 15 seconds to 1 minute), annealing (temperatures determined as discussed above, e.g. 60° C.; from 15 s to 2 minutes), and extension (72° C. for 1 minute) for a simple PCR (the extension and the annealing occurring at the same time, in a 60° C. step, for 1 min, in a q-PCR). An optional find extension step (useful in simple PCR) is generally carried out for about 4 minutes at 72° C., and may be followed by an indefinite (0-24 hour) step at 4° C.

The amplification or enrichment procedures of the present invention are performed in a PCR device such as a thermocycler, or more preferably under real-time reaction conditions in a real-time PCR device. Real-time reaction conditions further utilize a nucleic acid detection agent (e.g., dye or probe) in order to measure/detect the PCR product as it is produced.

The steps of the method are generally repeated for multiple cycles in order to get sufficient amplification of the target and reference sequences. In one embodiment, the steps of the method are repeated for 5-40 cycles and more preferably 10-40 cycles. The optimal number of cycles can be determined by one of ordinary skill in the art. Preferably, the present methods are performed in a PCR device, more preferably under real-time reaction conditions in a real-time detection PCR device, such as a Rotor-Gene Q 5plex HRM machine. In this embodiment, the reaction mixture may include a nucleic acid detection agent for quantifying and/or monitoring the amplification products of the reaction.

Analysis

The amplification of the target sequence can be followed by analysis of the amplified sequence, e.g. by a method to precisely determine the mutation(s) of the target sequence.

Once the amplification or enrichment of the target sequence is complete, the sample may thus be further processed, e.g., subjected to a sequencing reaction.

The amplified alleles may be further processed by a variety of procedures known in the art, including: MALDI-TOF, HR-Melting, Di-deoxy-sequencing, Single-molecule sequencing, second generation high throughput sequencing, pyrosequencing, RFLP, digital PCR, ARMS-PCR and quantitative-PCR.

Such analysis methods make it possible to identify the type of mutation(s) of the amplified target sequence.

The below Example illustrates the invention without limiting its scope.

EXAMPLE

Detection of Mutations in the IDH1 Gene

The invention described herein is a PCR-based method for the selective amplification of a DNA or cDNA target sequence that contains nucleotide variations in a selected region. The reaction mixture contains two generic PCR primers (a "Competitor PCR primer" and a "Second PCR primer") and a specific blocking oligonucleotide ("Oligo block").

This invention is illustrated by detection of mutations in the IDH1 gene.

IDH1 mutations at codon 132 have been found in gliomas and in hematological malignancies. Because mutant and wild-type sequences differ by the substitution of only one nucleotide (cf FIG. 2), a specific PCR method, which allows a selective discrimination between the wild-type and mutated sequences, is required.

Materials

Different designs for the Oligo block according to the present invention (with a nucleotide mismatch) were tested (RVS_R132Blc_d5 to RVS_R132Blc_d8, Table 1), and compared to corresponding Oligo blocks, without mismatch (RVS_R132Blc_d1 to RVS_R132Blc_d4, Table 1). All Oligo blocks contained a 3'Phosphate modification.

TABLE 1

Sequence and Tm of the different Oligo blocks tested for IDH1 R132 mutation detection. For the Oligo blocks RVS_R132Blc_d5 to RVS_R132Blc_d8, the mismatch nucleotide is in small letter. For each Oligo block, the variant position is underlined.

| Name | Sequence 5' 3' | Tm (° C.) | SEQ ID NO: |
|---|---|---|---|
| RVS_R132Blc_d1 | CCCCATAAGCA TGACGACCTAT GATGATA-P | 66.2 | SEQ ID NO: 8 |
| RVS_R132Blc_d2 | CCCCATAAGCA TGACGACCTAT GATG-P | 65.1 | SEQ ID NO: 9 |

TABLE 1-continued

Sequence and Tm of the different Oligo blocks tested for IDH1 R132 mutation detection. For the Oligo blocks RVS_R132Blc_d5 to RVS_R132Blc_d8, the mismatch nucleotide is in small letter. For each Oligo block, the variant position is underlined.

| Name | Sequence 5' 3' | Tm (° C.) | SEQ ID NO: |
|---|---|---|---|
| RVS_R132Blc_d3 | CCCATAAGCAT GACGACCTATG ATGA-P | 63.8 | SEQ ID NO: 10 |
| RVS_R132Blc_d4 | CCCATAAGCAT GACGACCTATG ATG-P | 62.4 | SEQ ID NO: 11 |
| RVS_R132Blc_d5 | CCCCATtAGCA TGACGACCTAT GATGATA-P | 63.9 | SEQ ID NO: 12 |
| RVS_R132Blc_d6 | CCCCATtAGCA TGACGACCTAT GATG-P | 62.8 | SEQ ID NO: 13 |
| RVS_R132Blc_d7 | CCCATtAGCAT GACGACCTATG ATGA-P | 62.2 | SEQ ID NO: 14 |
| RVS_R132Blc_d8 | CCCATtAGCAT GACGACCTATG ATG-P | 60.9 | SEQ ID NO: 15 |

Sequences of the Competitor PCR primer, the Second PCR primer and the Probe are presented in the table below. The probe was labeled with a fluorescent dye at its 5' end (FAM) and a quencher dye at its 3' end (TAMRA). These primers and probe were previously selected from several primers and probe designs.

TABLE 2

Sequence and Tm of the Competitor PCR primer, the Second PCR primer and the Probe. The common sequence between the Competitor PCR primer and the Oligo block is underlined.

| Name | Sequence 5' 3' | Tm (° C.) | SEQ ID NO: |
|---|---|---|---|
| Competitor PCR primer | TTGATCCC CATAAGCA TGA | 57.2 | SEQ ID NO: 16 |
| Second PCR_primer | CACGGTCT TCAGAGAA GCCATTAT | 63.1 | SEQ ID NO: 17 |
| Probe | 6FAM-TTT ACCCATCC ACTCACAA GCCGGG- TAMRA | 68.7 | SEQ ID NO: 18 |

Concentration of the PCR primers, the Oligo block & the Probe is listed below:

| Oligo | Concentration in reaction |
|---|---|
| Oligo block | 2 μM |
| PCR primers | 300 nM |
| Probe | 200 nM |

A Quantitect Probe PCR Kit (QIAGEN, Ref: 204345) was used for the amplification, and qPCR reactions were performed on a Rotor-Gene Q 5plex HRM machine (QIAGEN), using the following qPCR program:

TABLE 3

| | qPCR program |
|---|---|
| Hold | Temperature: 95° C. |
| | Time: 10 min |
| Cycling | 40 times |
| | 95° C. for 15 sec |
| | 60° C. for 60 sec with acquisition of FAM fluorescence in channel Green: Single |

For each Oligo block tested, the Oligo block was mixed with the Competitor PCR primer, the Second PCR Primer and the Probe. All these mixes were tested on samples containing genomic DNA (gDNA) extracted from formalin-fixed, paraffin-embedded (FFPE) tissue (IDH1 WT), in the absence or in the presence of plasmids containing an IDH1 R132H or an IDH1 R132C mutation. Three samples were tested: a 100% WT sample (negative for any IDH1 mutations), an IDH1 R132H sample with a level of mutation at 10%, and an IDH1 R132C sample with a level of mutation at 30%. The genomic DNA (gDNA) input per qPCR reaction was 25 ng for a final PCR volume of 25 μl.

Results

1. Performances Obtained Using Oligo Blocks According to the Invention, Compared to Oligo Blocks without Mismatch The table below shows the results obtained with the Oligo blocks according to the present invention, in comparison with Oligo blocks without mismatch.

TABLE 4

Ct (Cycle threshold) obtained on mutant (R132C and R132H) and WT samples with eight different Oligo block designs (four containing a mismatch, d5 to d8, and four with no mismatch, d1 to d4).

| | Ct value obtained with Oligo Block with mismatch (invention) | | | |
|---|---|---|---|---|
| Sample | Oligo Block RVS_R132Blc_d5 | Oligo Block RVS_R132Blc_d6 | Oligo Block RVS_R132Blc_d7 | Oligo Block RVS_R132Blc_d8 |
| WT | 38.67 | 37.18 | 38.49 | 36.75 |
| R132H | 30.04 | 29.55 | 29.62 | 29.36 |
| R132C | 35.25 | 31.31 | 28.74 | 28.27 |
| | Ct value obtained with Oligo Block without mismatch (prior art) | | | |
| Sample | Oligo Block RVS_R132Blc_d1 | Oligo Block RVS_R132Blc_d2 | Oligo Block RVS_R132Blc_d3 | Oligo Block RVS_R132Blc_d4 |
| WT | undetermined | undetermined | 41.52 | 42.68 |
| R132H | 40.13 | 41.12 | 33.81 | 32.3 |
| R132C | 39.83 | 38.27 | 40.73 | 40.17 |

Best results are obtained in a combination of the highest Ct on the WT sample and the lowest Ct for the mutant samples. As can be seen in Table 4, the addition of a nucleotide mismatch in the Oligo block allows obtaining lower Ct values on mutant samples, as compared to the corresponding Oligo block without mismatch. For instance, the Ct obtained for the IDH1 R132C mutant with the d7 Oligo block of the present invention was equal to 28.74, compared to 40.73 with the d3 Oligo block. Therefore, addition of the nucleotide mismatch in the Oligo block allows a better discrimination between the WT and mutant samples.

2. Sensitivity Test Results Using Oligo Blocks According to the Invention

Then, a Limit of Detection (LoD; NCCLS guideline CLSI EP17-A2) determination study was conducted using the d7 Oligo block.

Serial dilutions of the 6 IDH1 mutations, with mutant levels of 20%, 15%, 10%, 5% and 2% have been tested with the previously described PCR clamping system.

The analysis method is based on a ΔCt comparison between the Ct obtained with the reaction mix containing the Oligo block ($Ct_{mutant}$; only the mutant sequence is amplified) and the Ct sample obtained with the same reaction mix but without the Oligo block ($Ct_{total}$; mutant and WT sequences are amplified together)

$$\Delta Ct = Ct_{mutant} - Ct_{total}$$

ΔCt data have been generated for each of the 6 IDH1 mutations and each of the 5 mutation levels, (Table 5), and the LoD was determined based on a "precision profile approach", as described in the CLSI/NCCLS EP17-A guideline. As shown in table 5, mutation levels as low as 2.23% (depending on the type of mutation) can be detected, using the PCR method according to the present invention.

TABLE 5

LOD summary of 6 IDH1 mutations

| Assay | Sample | Mean ΔCt (n = 60) | Standard Deviation (SD) within-lab | LoD Estimation | Assay ΔCt cut-off | Sensitivity (Calculated LoD) |
|---|---|---|---|---|---|---|
| IDH1 R132 | R132H-20% | 2.44 | 0.37 | 5.50 | 5.34 | 2.32% |
| | R132H-15% | 2.85 | 0.32 | | | |
| | R132H-10% | 3.17 | 0.30 | | | |
| | R132H-5% | 4.36 | 0.36 | | | |
| | R132H-2% | 5.53 | 0.50 | | | |
| | R132C-20% | 3.32 | 0.56 | 5.34 | | 4.35% |
| | R132C-15% | 3.74 | 0.60 | | | |
| | R132C-10% | 4.28 | 0.55 | | | |
| | R132C-5% | 5.16 | 0.60 | | | |
| | R132C-2% | 6.35 | 0.62 | | | |
| | R132L-20% | 2.46 | 0.26 | 5.42 | | 2.30% |
| | R132L-15% | 2.83 | 0.33 | | | |
| | R132L-10% | 3.48 | 0.30 | | | |
| | R132L-5% | 4.39 | 0.41 | | | |
| | R132L-2% | 5.45 | 0.41 | | | |
| | R132G-20% | 2.39 | 0.31 | 5.61 | | 2.23% |
| | R132G-15% | 2.86 | 0.34 | | | |
| | R132G-10% | 3.22 | 0.36 | | | |
| | R132G-5% | 4.36 | 0.51 | | | |
| | R132G-2% | 5.45 | 0.43 | | | |
| | R132S-20% | 2.75 | 0.41 | 5.42 | | 2.75% |
| | R132S-15% | 3.15 | 0.47 | | | |
| | R132S-10% | 3.32 | 0.43 | | | |
| | R132S-5% | 4.65 | 0.34 | | | |
| | R132S-2% | 5.74 | 0.56 | | | |
| | R132V-20% | 2.57 | 0.27 | 5.56 | | 2.24% |
| | R132V-15% | 2.98 | 0.32 | | | |
| | R132V-10% | 3.59 | 0.31 | | | |
| | R132V-5% | 4.45 | 0.39 | | | |
| | R132V-2% | 5.38 | 0.45 | | | |

3. Performances Obtained Using Oligo Blocks According to the Invention, Compared to Peptide Nucleic Acid (PNA) Oligos The most common method to perform PCR clamp in order to detect variant sequences, uses PNA (Peptide Nucleic Acid) oligos. PNA oligos have the same function as 3' modified Oligo block, but, due to a higher DNA affinity, they usually allow a better discrimination between WT and variant sequences detection.

Four PNA oligos have been designed (see Table 6). They were mixed with the Competitor PCR primer, the Second PCR primer and the Probe, as previously described. The samples tested were a WT sample, and R132H & R132C mutated samples.

TABLE 6

Sequences of the PNA oligos.

| Sequence ID | 5' 3' Sequence |
| --- | --- |
| PNA_d1 (SEQ ID NO: 19) | TCATAGGTCGTCATGCT |
| PNA_d2 (SEQ ID NO: 20) | CATAGGTCGTCATG |
| PNA_d3 (SEQ ID NO: 21) | ATAGGTCGTCATG |
| PNA_d4 (SEQ ID NO: 22) | TAGGTCGTCAT |

Nucleotides in bold show the IDH1 variant sequence position.

The table below shows the results obtained with the four PNA oligos and with the d7 Oligo block, on the same samples.

TABLE 7

Ct results obtained on WT and IDH1 variant samples using PNA oligos (d1 to d4) or the d7 Oligo block.

| PNA oligo or Oligo block ID | Sample Name | Ct |
| --- | --- | --- |
| PNA d1 | WT | 37.89 |
|  | R132H | 43.17 |
|  | R132C | 28.33 |
| PNA d2 | WT | 38.95 |
|  | R132H | 32.29 |
|  | R132C | 27.85 |
| PNA d3 | WT | 37.43 |
|  | R132H | 29.54 |
|  | R132C | 27.43 |
| PNA d4 | WT | 31.31 |
|  | R132H | 29.14 |
|  | R132C | 27.7 |
| Oligo block RVS_R132Blc_d7 | WT | 38.49 |
|  | R132H | 29.62 |
|  | R132C | 28.74 |

Best results are obtained in combination where the highest Ct on the WT sample is associated to the lowest Ct for the mutant samples. As can be seen in Table 7, among PNA oligos, the d3 PNA oligo is the one showing the best performances, allowing the best discrimination between WT and variant sequences, and the d7 Oligo block shows performances that are comparable to the performances of the d3 PNA oligo (see Table 8 below).

TABLE 8

| Samples | Design Ct value | |
| --- | --- | --- |
|  | PNA_d3 | RVS_R132Blc_d7 |
| WT | 37.43 | 38.49 |
| R132H | 29.54 | 29.62 |
| R132C | 27.43 | 28.74 |

REFERENCES

Altschul et al, J. Mol. Biol. 1990 215:403-410

Altschul et al, Nucleic Acids Res. 199725:3389-3402

Dominguez P. L., Kolodney M. S. Wild-type blocking polymerase chain reaction for detection of single nucleotide minority mutations from clinical specimens. Oncogene. 2005; 24:6830-6834.

Mi-Ae Jang, Seung-Tae Lee, Young Lyun Oh, Sun Wook Kim, Jae Hoon Chung, Chang-Seok Ki, and Jong-Won Kim. Identification of a Rare 3 bp BRAF Gene Deletion in a Thyroid Nodule by Mutant Enrichment with 3'-Modified Oligonucleotides Polymerase Chain Reaction Ann Lab Med. 2012 May; 32(3): 238-241.

Lee S T, Kim J Y, Kown M J, Kim S W, Chung J H, Ahn M J, Oh Y L, Kim J W, Ki C S. Mutant enrichment with 3'-modified oligonucleotides a practical PCR method for detecting trace mutant DNAs J Mol Diagn. 2011 November; 13(6):657-68.

Li J., Wang L., Mamon H., Kulke M. H., Berbeco R., Makrigiorgos G. M. Replacing PCR with COLD-PCR enriches variant DNA sequences and redefines the sensitivity of genetic testing. Nat Med. 2008; 14:579-584.

Sun X., Hung K., Wu L., Sidransky D., Guo B. Detection of tumor mutations in the presence of excess amounts of normal DNA. Nature Biotechnol. 2002; 20:186-189.

Wetmur, J. G. DNA probes: applications of the principles of nucleic acid hybridization. Crit Rev Biochem Mol Biol 1991. 26: 227-259

The invention claimed is:

1. An in vitro method for selectively amplifying a target DNA sequence from a nucleic acid sample, which method comprising
   a. providing a nucleic acid sample suspected of comprising at least one target DNA sequence that differs from a reference DNA sequence at at least one target mutation present in a target mutation site;
   b. adding:
      i) a forward primer oligonucleotide and a reverse primer oligonucleotide, which are fully complementary to a primer binding site, wherein the primer binding site comprises a portion of the reference DNA sequence surrounding the target mutation site, and do not bind to the target mutation site in the reference DNA sequence or the target mutation site in the target DNA sequence,
      ii) a blocking oligonucleotide, which is designed to compete with one of the primer oligonucleotides and is modified so that it cannot be extended by polymerase and wherein the blocking oligonucleotide is fully complementary to the target mutation site of the reference DNA sequence and comprises at least one mismatch with the reference DNA sequence outside the target mutation site,
   so as to form a reaction mixture;
   c. subjecting the reaction mixture to amplification by polymerase chain reaction (PCR), whereby the primer oligonucleotides are extended so as to selectively amplify said target DNA sequence.

2. The method of claim 1, wherein the target mutation site comprises a substitution of one or several nucleotides, a deletion of one or several nucleotides, or an insertion of one or several nucleotides.

3. The method of claim 2, wherein the target mutation site comprises a single nucleotide substitution.

4. The method of claim 1, wherein said mismatch in the blocking oligonucleotide is located upstream from the target mutation site.

5. The method of claim 1, wherein the 3'-end of the blocking oligonucleotide is modified to inhibit extension by polymerase.

6. The method of claim 5, wherein the 3'-end on the blocking oligonucleotide comprises a C3 spacer, a C6 amine or a phosphate group.

7. The method of claim 1, wherein the blocking oligonucleotide is one of single stranded DNA, RNA, peptide nucleic acid or locked nucleic acid.

8. The method of claim 1, wherein the blocking oligonucleotide sequence is designed to have a higher melting temperature (Tm) and/or is added at a higher concentration than the primer oligonucleotide it competes with.

9. The method of claim 1, wherein the blocking oligonucleotide is added at a concentration that is at least 4 or 5 times higher than the concentration of the primer oligonucleotide it competes with.

10. The method of claim 1, wherein said reaction mixture further contains a nucleic acid detection dye.

11. The method of claim 1, wherein said reaction mixture further contains a probe.

12. The method of claim 11, wherein the probe is a hydrolysis probe.

13. The method of claim 1, wherein the PCR is a quantitative PCR.

14. A method for detecting and/or determining a target mutation in a nucleic acid sample, which method comprises subjecting a nucleic acid sample suspected of comprising at least one target DNA sequence that differs from a reference DNA sequence at at least one target mutation site, to the amplification method according to claim 1, and detecting and/or determining the target mutation of the target DNA sequence that has been amplified.

15. The method of claim 14, comprising determining the target mutation of the target DNA sequence that has been amplified by using one or more of the methods selected from the group consisting of: MALDI-TOF, HR-Melting, Di-deoxy-sequencing, Single molecule sequencing, pyrosequencing, Second generation high-throughput sequencing, SSCP, RFLP, dHPLC, digital PCR, ARMS-PCR and quantitative-PCR.

16. The method of claim 11, wherein the probe is a labeled probe.

17. The method of claim 1, wherein the at least one mismatch with the reference DNA sequence outside the target mutation site is located in a part of the blocking oligonucleotide that overlaps with the primer oligonucleotide with which it competes.

* * * * *

SEQUENCE LISTING

```
<160> NUMBER OF SEQ ID NOS: 22

<210> SEQ ID NO 1
<211> LENGTH: 68
<212> TYPE: DNA
<213> ORGANISM: Homo sapiens

<400> SEQUENCE: 1
gagtggatgg gtaaaaccta tcatcatagg tcgtcatgct tatggggatc aagtaagtca      60
tgttggca                                                              68

<210> SEQ ID NO 2
<211> LENGTH: 68
<212> TYPE: DNA
<213> ORGANISM: Homo sapiens

<400> SEQUENCE: 2
gagtggatgg gtaaaaccta tcatcatagg tcatcatgct tatggggatc aagtaagtca      60
tgttggca                                                              68
```

<210> SEQ ID NO 3
<211> LENGTH: 68
<212> TYPE: DNA
<213> ORGANISM: Homo sapiens

<400> SEQUENCE: 3
gagtggatgg gtaaaaccta tcatcatagg ttgtcatgct tatggggatc aagtaagtca    60
tgttggca                                                              68

<210> SEQ ID NO 4
<211> LENGTH: 68
<212> TYPE: DNA
<213> ORGANISM: Homo sapiens

<400> SEQUENCE: 4
gagtggatgg gtaaaaccta tcatcatagg tagtcatgct tatggggatc aagtaagtca    60
tgttggca                                                              68

<210> SEQ ID NO 5
<211> LENGTH: 68
<212> TYPE: DNA
<213> ORGANISM: Homo sapiens

<400> SEQUENCE: 5
gagtggatgg gtaaaaccta tcatcatagg tggtcatgct tatggggatc aagtaagtca    60
tgttggca                                                              68

<210> SEQ ID NO 6
<211> LENGTH: 68
<212> TYPE: DNA
<213> ORGANISM: Homo sapiens

<400> SEQUENCE: 6
gagtggatgg gtaaaaccta tcatcatagg tcttcatgct tatggggatc aagtaagtca    60
tgttggca                                                              68

<210> SEQ ID NO 7
<211> LENGTH: 68
<212> TYPE: DNA
<213> ORGANISM: Homo sapiens

<400> SEQUENCE: 7
gagtggatgg gtaaaaccta tcatcatagg tgttcatgct tatggggatc aagtaagtca    60
tgttggca                                                              68

<210> SEQ ID NO 8
<211> LENGTH: 29
<212> TYPE: DNA
<213> ORGANISM: Artificial
<220> FEATURE:
<223> OTHER INFORMATION: OligoBlock RVS_R132B1c_d1

<400> SEQUENCE: 8
ccccataagc atgacgacct atgatgata                                      29

<210> SEQ ID NO 9
<211> LENGTH: 26
<212> TYPE: DNA
<213> ORGANISM: Artificial
<220> FEATURE:

```
<223> OTHER INFORMATION: Oligo block RVS_R132Blc_d2

<400> SEQUENCE: 9
ccccataagc atgacgacct atgatg                                          26

<210> SEQ ID NO 10
<211> LENGTH: 26
<212> TYPE: DNA
<213> ORGANISM: Artificial
<220> FEATURE:
<223> OTHER INFORMATION: Oligo Block RVS_132Blc_d3

<400> SEQUENCE: 10
cccataagca tgacgaccta tgatga                                          26

<210> SEQ ID NO 11
<211> LENGTH: 25
<212> TYPE: DNA
<213> ORGANISM: Artificial
<220> FEATURE:
<223> OTHER INFORMATION: Oligo Block RVS_R132Blc_d4

<400> SEQUENCE: 11
cccataagca tgacgaccta tgatg                                           25

<210> SEQ ID NO 12
<211> LENGTH: 29
<212> TYPE: DNA
<213> ORGANISM: Artificial
<220> FEATURE:
<223> OTHER INFORMATION: Oligo Block RVS_R132Blc_d5

<400> SEQUENCE: 12
ccccattagc atgacgacct atgatgata                                       29

<210> SEQ ID NO 13
<211> LENGTH: 26
<212> TYPE: DNA
<213> ORGANISM: Artificial
<220> FEATURE:
<223> OTHER INFORMATION: Oligo block RVS_R132Blc_d6

<400> SEQUENCE: 13
ccccattagc atgacgacct atgatg                                          26

<210> SEQ ID NO 14
<211> LENGTH: 26
<212> TYPE: DNA
<213> ORGANISM: Artificial
<220> FEATURE:
<223> OTHER INFORMATION: Oligo BlockRVS_R132Blc_d7

<400> SEQUENCE: 14
cccattagca tgacgaccta tgatga                                          26

<210> SEQ ID NO 15
<211> LENGTH: 25
<212> TYPE: DNA
<213> ORGANISM: Artificial
<220> FEATURE:
<223> OTHER INFORMATION: Oligo Block RVS_R132Blc_d8

<400> SEQUENCE: 15
cccattagca tgacgaccta tgatg                                           25
```

```
<210> SEQ ID NO 16
<211> LENGTH: 19
<212> TYPE: DNA
<213> ORGANISM: Artificial
<220> FEATURE:
<223> OTHER INFORMATION: competitor PCR primer

<400> SEQUENCE: 16
ttgatcccca taagcatga                                                19

<210> SEQ ID NO 17
<211> LENGTH: 24
<212> TYPE: DNA
<213> ORGANISM: Artificial
<220> FEATURE:
<223> OTHER INFORMATION: second PCR primer

<400> SEQUENCE: 17
cacggtcttc agagaagcca ttat                                          24

<210> SEQ ID NO 18
<211> LENGTH: 25
<212> TYPE: DNA
<213> ORGANISM: Artificial
<220> FEATURE:
<223> OTHER INFORMATION: probe

<400> SEQUENCE: 18
tttacccatc cactcacaag ccggg                                         25

<210> SEQ ID NO 19
<211> LENGTH: 17
<212> TYPE: DNA
<213> ORGANISM: Artificial
<220> FEATURE:
<223> OTHER INFORMATION: PNA_d1 oligonucleotide

<400> SEQUENCE: 19
tcataggtcg tcatgct                                                  17

<210> SEQ ID NO 20
<211> LENGTH: 14
<212> TYPE: DNA
<213> ORGANISM: Artificial
<220> FEATURE:
<223> OTHER INFORMATION: PNA_d2 oligonucleotide

<400> SEQUENCE: 20
cataggtcgt catg                                                     14

<210> SEQ ID NO 21
<211> LENGTH: 13
<212> TYPE: DNA
<213> ORGANISM: Artificial
<220> FEATURE:
<223> OTHER INFORMATION: PNA_d3 oligonucleotide

<400> SEQUENCE: 21
ataggtcgtc atg                                                      13

<210> SEQ ID NO 22
<211> LENGTH: 11
<212> TYPE: DNA
<213> ORGANISM: Artificial
<220> FEATURE:
<223> OTHER INFORMATION: PNA_d4 oligonucleotide
```

```
<400> SEQUENCE: 22
taggtcgtca t                                                          11
```